United States Patent [19]

Mareschal et al.

[11] Patent Number: 4,725,556

[45] Date of Patent: Feb. 16, 1988

[54] PROCESS OF IMMUNOASSAY OF A SUBSTANCE IN A LIQUID SAMPLE CONTAINING A SIMILAR SUBSTANCE

[76] Inventors: Jean-Claude Mareschal, 196, av. de la Veequee, 5730 Malonne; Pierre L. Masson, 107 Av. Emile Vandervelde, 1200 Brussels, both of Belgium

[21] Appl. No.: 734,166

[22] Filed: May 15, 1985

[30] Foreign Application Priority Data

May 15, 1984 [BE] Belgium .................... 0/212939

[51] Int. Cl.⁴ ............... G01N 33/546; G01N 33/555; G01N 33/563
[52] U.S. Cl. ........................... 436/500; 436/512; 436/520; 436/533; 436/534; 436/817; 436/818; 436/825
[58] Field of Search ............ 436/507, 512, 536, 500, 436/520, 533, 534, 817, 818, 825; 435/7

[56] References Cited

U.S. PATENT DOCUMENTS

| | | | |
|---|---|---|---|
| 4,256,629 | 3/1981 | Bahl | 436/818 |
| 4,397,960 | 8/1983 | Moussebois et al. | 436/512 |
| 4,459,359 | 6/1984 | Neurath | 436/825 |

FOREIGN PATENT DOCUMENTS

| | | |
|---|---|---|
| 0038181 | 10/1981 | European Pat. Off. . |
| 0051985 | 5/1982 | European Pat. Off. . |
| 0148166 | 7/1985 | European Pat. Off. . |

OTHER PUBLICATIONS

Masson, U.S. Application Serial No. 747,174, filed 6/1985.

"Structure of an Exophthalmos-producing Factor Derived from Thyrotropin by Partial Pepsin Digestion", by L. D. Kohn and R. J. Winand, The Journal of Biological Chemistry, No. 16, pp. 6503–6508, 1975.

*Primary Examiner*—Sidney Marantz
*Assistant Examiner*—David A. Saunders
*Attorney, Agent, or Firm*—Cushman, Darby & Cushman

[57] ABSTRACT

A process of immunoassay of a selected substance in a liquid sample containing one or more other non-selected substances, each of these substances being comprised of at least two structurally different chains, the process comprising among others addition of a dissociating agent, such as for example a proteolytic enzyme, to the sample, mixing of the so-obtained liquid, inactivation of the dissociating agent, addition of antiserums, and determination of the amount of this selected substance in the liquid sample.

16 Claims, No Drawings

PROCESS OF IMMUNOASSAY OF A SUBSTANCE IN A LIQUID SAMPLE CONTAINING A SIMILAR SUBSTANCE

This invention relates to a process of immunoassay of a selected substance in a liquid sample, for example a biological liquid containing one or more other non-selected substances which are susceptible to interfere with the assay of the selected substance.

As it is known, some substances, such as animal and human hormones, comprise at least two structurally different chains or fragments which are weakly bonded together, one of said chains or one of said fragments being immunologically common and the other one being immunologically distinct for each substance. The assay of these substances very often is particularly important in diagnostics However, some cross-reactions very often appear between the substance to be assayed and other substances which consequently interfere with the assay of this first substance and which make false the results of the assay. Although it is possible to induce a highly specific antserum of the substance to be assayed, by using the structurally distinct chain or fragment of this latter only, some cross-reactivity always remains existent, which makes false the results of the assay of the concerned substance. However, this reactivity can still be reduced by using antiserum against the molecule or substance which structurally is the closest to the substance to be assayed and against which this antiserum is directed. Antibodies contained in the antiserum and which are not totally specific to the substance to be assayed will then bond to the excess of this other substance and may be separated from the antiserum. Such a technique is efficient and gives relatively good results, in particular when the substance of treatment is, for example, human chorionic gonadotropin (hCG), the cost of which is not excessive. However, when compounds such as follicle-stimulating hormone (FSH), luteinizing hormone (LH) or thyroid-stimulating hormone (TSH) are to be used, this process is no longer interesting, the cost for these substances being excessive.

The purpose of the present invention consequently consists in remedying the drawbacks of the known assay processes and in providing a process allowing to improve the specificity of the immunoassay of a selected substance in a liquid, such as a biological liquid containing one or more other non-selected substances which are susceptible to interfere with the assay of the selected substance, without it being necessary to use a purified cross-reacting substance, the cost of which is extremely high in most cases. The process according to the invention may be used for assaying any kind of substances as far as this substance and the other substance or substances susceptible to interfere with the assay are comprised of at least two structurally different chains or fragments, one of these chains or one of these fragments being immunologically common while the other one is immunologically distinct.

To this end, according to the invention, a dissociating agent selected from the group comprising proteolytic agents, agents breaking disulfide bridges, chaotropic agents and mixtures of at least two of these agents is added to the liquid sample in order to split the selected substance to be assayed into at least its two chains or fragments, the non-selected substance or substances being also split into at least its or their two chains or fragments, the so obtained liquid is mixed, the dissociating agent is inactivated, this mixture is added with an antiserum directed againt the immunologically common chain or fragment of the selected substance and of the non-selected substance or substances, an antiserum directed against the immunologically distinct chain or fragment of the selected substance to be assayed is added to the resulting solution, and the amount of this selected substance in the liquid sample is determined.

According to a particular embodiment of the process according to the invention, the selected substance and the non-selected substance or substances are hormones, such as the thyroid-stimulating hormone (TSH), the follicle-stimulating hormone (FSH), the luteinizing hormone (LH) and the human chorionic gonadotropin (hCG), the immunologically common and distinct chains being in such a case comprised of the alpha and beta chains respectively.

Examples of proteolytic agents are proteolytic enzymes, such as pepsin, papain and trypsin, the pepsin being particularly suitable to this end. Examples of agents breaking disulfide bridges are substances having a reducing activity, such as mercaptoethanol and dithiotreitol. Examples of chaotropic agents are urea, guanidine hydrochloride and ammonium thiocyanate.

According to another particular embodiment of the invention, the amount of the selected substance in the liquid sample is determined by a process of agglutination of particles, the amount of selected substance being determined as a function of the agglutination or non-agglutination level of finely divided particles, said particles being preferably made of acrylamide or polystyrene or comprised of red blood cells. Particles of acrylamide, polystyrene or any other polymer are generally called "latex".

Other details and particularities of the invention will become apparent from the following description given by way of a non-limitative example of some particular embodiments of the invention.

As already mentioned hereinabove, the present invention provides a process for immunoassaying a selected substance, such as for example a hormone of animal or human origin, in a biological liquid containing one or more other non-selected substances which are susceptible to interfere with the assay of the substance to be assayed, these other substances being also possibly hormones of animal or human origin, for diagnostic purposes, without cross-reactions able to make false the results of the assay of the selected substance. Extremely important hormones for a diagnostic, which are difficult to be assayed without cross-reactions appearing are, as already mentioned hereinbefore, thyroid-stimulating hormone (TSH), follicle-stimulating hormone (FSH), luteinizing hormone (LH) and human chorionic gonadotropin (hCG). Each of these substances is composed of two parts, loosely bonded together and known as alpha and beta chains, the alpha chain of these substances being immunologically common, while the beta chain is immunologically distinct for each substance.

According to the invention, a dissociating agent, such as for example a proteolytic agent which may be pepsin, papain or trypsin is added to the biological liquid containing the substance to be assayed, this substance to be assayed and the substance or the substances susceptible to interfere with the assay being broken by digestion by means of this enzyme into at least their two structurally different chains. In the case of above-mentioned hormones, the digestion process with pepsin such as described in the European Pat. No. 51,985 could for example be used, this process splitting alpha and beta chains of each hormone. Digestion with proteolytic enzyme must be such that the selected substance as well as the non-selected substance or substances must at least be split into their two chains, the digestion may however be extended so as to more extensively divide both structurally different chains into fragments. As soon as splitting or fragmentation of both chains is ended, the so-obtained liquid is mixed for example for a period of about 5 to 15 minutes, the proteolytic enzyme is inactivated for example by means of a neutralizing agent, raising pH of the mixture to a value of about 7 to 9. Then, the mixture is added with an antiserum directed against the immunologically common chain of the selected substance and of the non-selected substance or substances, and then an antiserum directed against the immunologically distinct chain of the selected substance to be assayed is added to the resulting solution. For example, the alpha chain could be bonded by means of an antiserum directed against any of the four hormones such as previously cited, all of them comprising the same alpha chain. As an example, according to the invention, a human serum sample could be treated with pepsin, which splits the hCG molecule into its alpha and beta chains or into smaller fragments according to a manner known per se (see for example Kohn, L. D. and Winand R. J., Biol. Chem. 16, 6503–6508, 1975), then mixing the so-obtained solution for a period of about 5 to 15 minutes and, after pepsin inactivation, addition of an anti-TSH antiserum, the antibodies of which react with the alpha chain or fragments thereof of the hormones contained in the serum sample, namely LH, FSH, hCG and TSH. If then an antiserum directed against the beta chain of hCG is added, the only free antigens are the beta chain of this hormone. Therefore, the specificity of this hormone assay is highly increased. After the antiserums have been added, generally the so-obtained solution is incubated under stirring at a temperature of about 37° C. for a period of about 15 to 60 minutes. Due to the fact that large amounts of antiserum can be induced from a relatively small amount of pure substance, the process according to the invention is thus a process allowing to substantially increase the specificity of a substance immunoassay, this process being extremely simple to be used and economic. Obviously, as already mentioned previously, it could be possible to use other agents than proteolytic agents as dissociating agents, for example agents breaking disulfide bridges or choatropic agents, which act to break hydrogen and hydrophobe bindings. In this respect, as non-limitative examples, one can mention as agents breaking disulfide bridges, substances having a reducing activity, such as mercaptoethanol and dithiotreitol, and as chaotropic agents, urea, guanidine hydrochloride and ammonium thiocyanate.

According to the invention, the amount of selected substance in the biological liquid is preferably determined, after addition of the antiserum, by means of an agglutination technique of particles, the amount of selected substance being determined as a function of the agglutination or non-agglutination level of finely divided particles which, as already mentioned hereinbefore, are preferably acrylamide or polystyrene particles or red blood cells. Hereinafter assay of hCG will be described as a non-limitative example, when using latex particle counting immunoassay (PACIA), although as known by the ones skilled in the art this technique may also be applied to a large number of other immunoassay forms, such as radioimmunoassay, enzymoimmunoassay, fluoroimmunoassay and the like.

The hCG measurement is very important in the determination of pregnancy at a very early stage. The determination of the hCG content is also important for a rapid diagnostic of an ectopic pregnancy in order to prevent a tube rupture or strong haemorrhages. Finally, as a tumour marker, the hCG measurement is very often the only test which may be made to determine the patent response to chemotherapy for a choriocarcinoma. The need for an extremely sensitive and precise assay is therefore obvious. Unfortunately, in many women, particularly during the menopausal period, the LH level can be so high as to give false positive results in respect to the hCG content.

EXAMPLE

An antiserum directed against hCG (supplied by Dakopatts) was reduced into F (ab')$_2$ fragments by pepsin digestion and these fragments were bound to latex [latex F (ab')$_2$] according to the process described in the U.S. Pat. No. 4,397,960. The latex thus acts as a support for F (ab')$_2$ fragments of the antibodies, which are directed against hCG. On the other hand, in an automated analyser, 30 μl of the sample to be analysed were diluted with 300 μl of pepsin reaction mixture (10 mgr/ml of 0.3 N HCl) and the mixture was incubated at room temperature for 5 minutes under continuous stirring. Then, pH of the mixture was increased to 7.5–8 by addition of 60 μl of 1 M Tris. To this mixture, 10 μl of a rabbit anti-TSH antiserum (IgG fraction: 10 mgr/ml) and a 0.05% suspension of latex covered with F(ab')$_2$ fragments prepared as hereinbefore mentioned were then added. This rabbit antiserum as source of antibodies directed against the alpha chain of hormones contained in the sample was obtained by intradermal bimonthly injection of 20 μgr of TSH in complete Freund's adjuvant. The entire mixture was then incubated at 37° C. for 35 minutes under continuous stirring. The reaction was stopped by automatic addition of 1.0 ml of saline solution buffered with glycine containing 0.1% of Tween non-ionic detergent and, after a further 20-fold dilution, the non-agglutinated latex particles were counted. Counting of non-agglutinated latex particles gives in fact a measure of the agglutinated latex amount which, in turn, allows to determine the hCG amount in the sample to be analysed. Obviously, the agglutinated latex amount could also be measured directly. By assaying four different hCG concentrations (5, 20, 50 and 200 mIU/ml), ten times each, the following intra-assay precision was obtained.

| hCG conc. (mIU/ml) | Intra-assay precision S.D.* (mIU/ml) | C.V.** % |
|---|---|---|
| 6,53 | 0,46 | 7,0 |
| 19,45 | 0,49 | 2,5 |
| 41,20 | 1,13 | 2,7 |
| 149,20 | 8,32 | 5,6 |

By also assaying four different hCG concentrations (10, 20, 50 and 200 mIU/ml), each day for 15 days, the following intra-assay precision was obtained:

| hCG conc. (mIU/ml) | Intra-assay precision | |
|---|---|---|
| | S.D.* (mIU/ml) | C.V.** % |
| 10,2 | 0,55 | 5,5 |
| 20,2 | 1,59 | 7,8 |
| 50,2 | 3,79 | 7,5 |
| 198,5 | 9,87 | 4,9 |

*S.D. = standard deviation
**C.V. = coefficient of variation

Recovery

If 10, 50 and 200 mIU/ml of hCG are added to male serum, namely deprived of hCG, recoveries were 87.9%, 103.4% and 103.4% respectively, these being satisfactory results which show that other hormones contained in the serum have not interfered with hCG.

Correlation with radioimmunoassay made on clinical samples revealed a correlation coefficient of 0.96 with a regression line of $Y = -11.2 + 1.06X$ for 15 samples, whose concentration varies from 8 mIU/ml to 1.850 mIU/ml, which is a quite satisfactory result.

In order to test the efficiency of the treatment with anti-TSH antiserum, 10 serums of menopaused women were used, which by radioimmunoassay (RIA) had shown very high LH contents, for the measurement of hCG.

| LH content (mIU/ml) as measured by RIA | hCG content without anti-TSH (mIU/ml) as measured by PACIA | hCG content with anti-TSH as measured by PACIA |
|---|---|---|
| 117 | 22 | 9 |
| 74 | 12,5 | 3,5 |
| 232 | 25 | 10 |
| 77 | 15 | 6,5 |
| 62 | 11 | 3,5 |
| 74 | 7,2 | 1 |
| 82 | 9 | 6 |
| 77 | 21 | 7,4 |
| 91 | 24 | 9,2 |
| 135 | 13,2 | 1 |

In the above-mentioned assay, a hCG concentration of 25 mIU/ml is regarded as a true positive result, that is to say that in this case the women should be considered as pregnant. As it may be seen from the results obtained without anti-TSH antiserum, at least one of the 10 samples (the first one) should have been considered as positive, while two others of these samples (22 and 24 mIU/ml) would probably have been recalled and reanalyzed, results being doubtful. In fact, when assaying hCG content of same serums with incorporation of antiTSH according to the process of the invention, it may be seen that no sample is positive, all the hCG values being substantially lower than 25.

It has to be understood that this invention is in no way limited to the above-described embodiments and that many modifications may be brought thereto without departing from the scope of the present patent.

We claim

1. A process of immunoassay of a selected substance in a liquid sample containing at least one other substance which can interfere with the assay of said selected substance, said selected substance and said other substance each being composed of at least two structurally different fragments, a first fragment of said selected substance being immunologically the same as a first fragment of said other substance, a second fragment of said selected substance being immunologically distinct from any fragment of said other substance, wherein said process comprises the steps of:

adding a dissociating agent selected from the group consisting of proteolytic agents, agents capable of breaking disulfide bridges, chaotropic agents, and mixtures thereof, to said liquid sample in order to split said selected substance into at least two fragments, said other substance being also split into at least two fragments, inactivating said dissociating agent, adding to said sample liquid an antiserum directed against said first fragment of said selected substance and said first fragment of said other substance, adding an antiserum directed against the immunologically distinct fragment of said selected substance to said liquid sample, and determining the amount of said selected substance in said liquid sample.

2. A process as claimed in claim 1, wherein said selected substance and said other substance are hormones.

3. A process as claimed in claim 2, wherein said selected substance is a hormone selected from the group consisting of the thyroid-stimulating hormone (TSH), the follicle-stimulating hormone (FSH), the luteinizing hormone (LH) and the human chorionic gonadotropin (hCG).

4. A process as claimed in claim 3, wherein said selected substance to be assayed is the human chorionic gonadotropin.

5. A process as claimed in claim 2, wherein said first fragment and said second fragment of said hormones are comprised of the alpha and beta chains respectively.

6. A process as claimed in claim 1, wherein the liquid sample is a biological liquid.

7. A process as claimed in claim 1, wherein after addition of the dissociating agent, the resulting liquid is mixed for a period of about 5 to 15 minutes.

8. A process as claimed in claim 1, wherein the dissociating agent is inactivated by raising the mixture pH to a value of about 7 to 9.

9. A process as claimed in claim 1, wherein after addition of the antiserums, the so-obtained solution is concentrated under stirring at a temperature of about 37° C. for a period of about 15 to 60 minutes.

10. A process claimed in claim 1, wherein the dissociating agent is a proteolytic enzyme.

11. A process as claimed in claim 10, wherein the proteolytic agent is selected from the group consisting of pepsin, papain and trypsin.

12. A process as claimed in claim 1, wherein the dissociating agent is an agent breaking the disulfide bridges, selected from the group consisting of mercapto ethanol and dithiotreitol.

13. A process as claimed in claim 1, wherein the dissociating agent is a chaotropic agent, selected from the group consisting of urea, guanidine hydrochloride and ammonium thiocyanate.

14. A process as claimed in claim 1, wherein the amount of said selected substance in the liquid sample is determind by an agglutination technique of particles as a function of the agglutination or non-agglutination level of finely divided particles.

15. A process as claimed in claim 14, wherein latex particles or red blood cells are used as finely divided particles.

16. A process as claimed in claim 14, wherein said selected substance is the human chorionic gonadotropin (hCG), the antiserum directed against said first fragment is an anti-TSH rabbit antiserum, and the antiserum directed against said second fragment is a latex suspension coated with F(ab')$_2$ fragments.

* * * * *